(12) United States Patent
Van Sickle et al.

(10) Patent No.: US 9,314,015 B2
(45) Date of Patent: Apr. 19, 2016

(54) METHOD AND APPARATUS FOR PREVENTION OF THERMO-MECHANICAL FRACTURING IN VITRIFIED TISSUE USING RAPID COOLING AND WARMING BY PERSUFFLATION

(71) Applicant: Arigos Biomedical, Inc., Mountain View, CA (US)

(72) Inventors: Stephen Van Sickle, Sunnyvale, CA (US); Tanya Jones, Sunnyvale, CA (US)

(73) Assignee: Arigos Biomedical, Inc., Santa Clara, CA (US)

( * ) Notice: Subject to any disclaimer, the term of this patent is extended or adjusted under 35 U.S.C. 154(b) by 0 days.

(21) Appl. No.: 13/936,069

(22) Filed: Jul. 5, 2013

(65) Prior Publication Data

US 2014/0011182 A1    Jan. 9, 2014

Related U.S. Application Data

(60) Provisional application No. 61/805,875, filed on Mar. 27, 2013, provisional application No. 61/668,995, filed on Jul. 6, 2012, provisional application No. 61/668,998, filed on Jul. 6, 2012.

(51) Int. Cl.
*A01N 1/02* (2006.01)

(52) U.S. Cl.
CPC .............. *A01N 1/021* (2013.01); *A01N 1/0284* (2013.01); *A01N 1/0289* (2013.01)

(58) Field of Classification Search
CPC ..... A01N 1/02; A01N 1/0284; A01N 1/0226; A01N 1/021; A01N 1/0289
See application file for complete search history.

(56) References Cited

U.S. PATENT DOCUMENTS

| 4,471,629 A | 9/1984 | Toledo-Pereyra |
| 6,274,303 B1 * | 8/2001 | Wowk et al. ................... 435/1.3 |
| 2010/0330547 A1 | 12/2010 | Tempelman et al. |

FOREIGN PATENT DOCUMENTS

| CN | 1173220 A | 2/1998 |
| CN | 1505474 A | 6/2004 |

(Continued)

OTHER PUBLICATIONS

Suszynski, T.M. et al. "Persufflation (or gaseous oxygen perfusion) as a method of organ preservation." Cryobiology, 2012, vol. 64, Issue 3, pp. 125-143.

(Continued)

*Primary Examiner* — Robert Yamasaki
*Assistant Examiner* — Charles Zoltan Constantine
(74) *Attorney, Agent, or Firm* — David H. Jaffer; Pillsbury Winthrop Shaw Pittman LLP

(57) ABSTRACT

A method and apparatus are disclosed for avoiding fracturing, e.g., thermo-mechanical fracturing, in vitrified biological systems via rapid cooling and/or warming persufflation techniques, by reducing the domain size of fracturing and by reducing thermal gradients. Also disclosed is a system adapted to rapidly cool and warm vitrifiable vascular biological tissue by persufflation, significantly reducing cryoprotectant toxicity from that of surface cooled tissue, in which the system is constructed and configured to use one or more of helium gas, hydrogen gas, neon gas, argon gas, krypton gas, xenon gas, oxygen gas, or various gaseous compounds. The system can be operated under pressure to increase the density and heat capacity of the gas relative to its density and heat capacity at atmospheric pressure and to cool the gas by one or more of mechanical action and by the phase change of a material such as a cryogenic gas or solid.

8 Claims, 4 Drawing Sheets

Persufflation Apparatus

(56) References Cited

FOREIGN PATENT DOCUMENTS

| JP | 2008222640 A | 9/2008 |
| WO | WO9507611 A1 | 3/1995 |

OTHER PUBLICATIONS

International Search Report dated Oct. 14, 2013 in corresponding PCT Application No. PCT/US2013/049477.

* cited by examiner

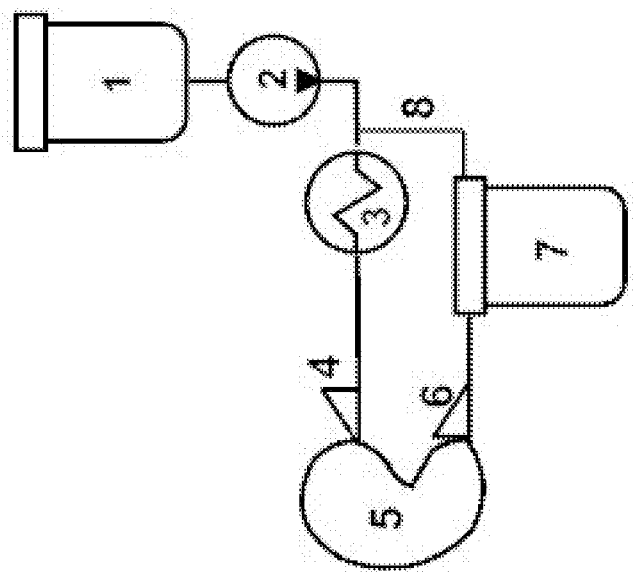
Figure 1: Simplified Perfusion Circuit

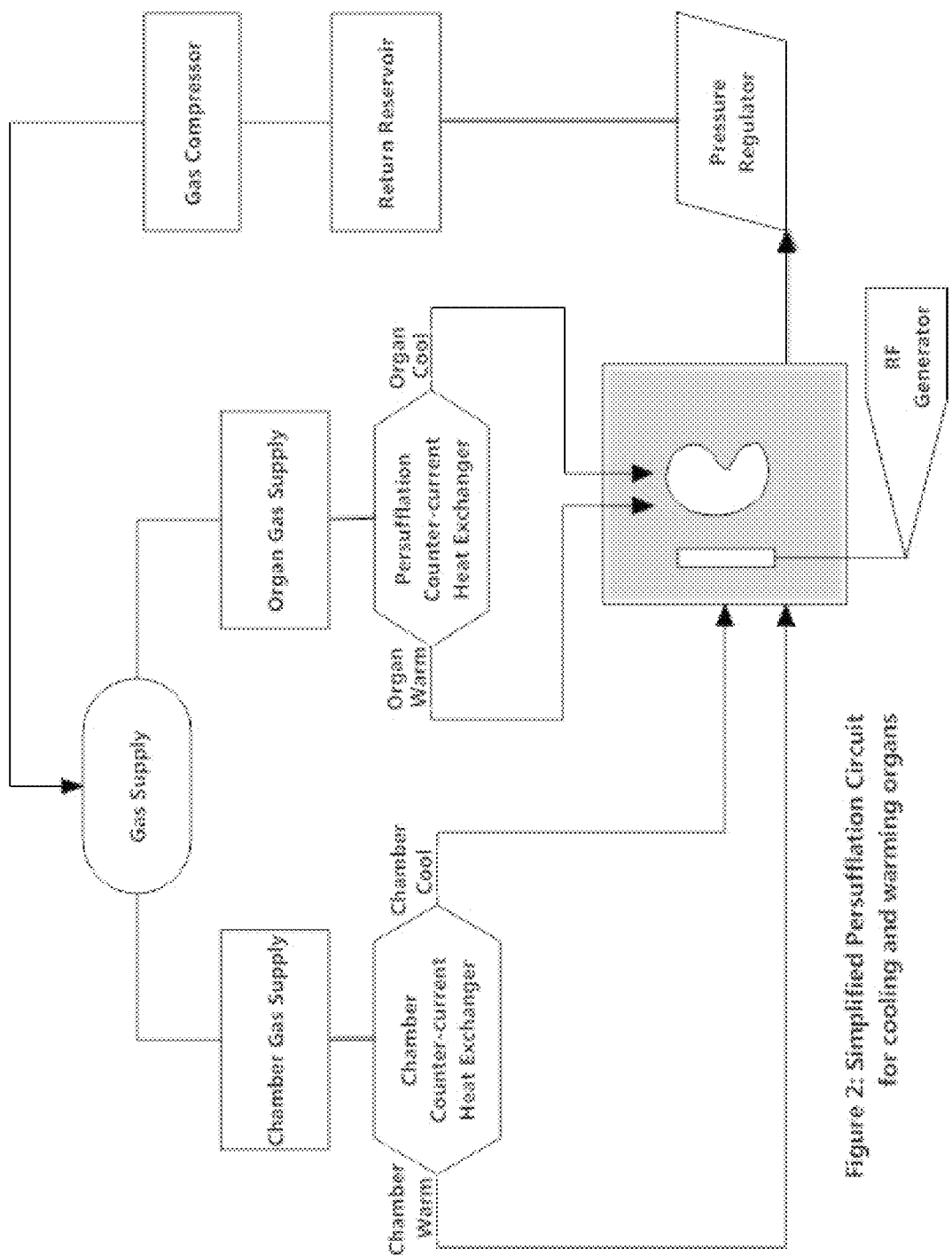

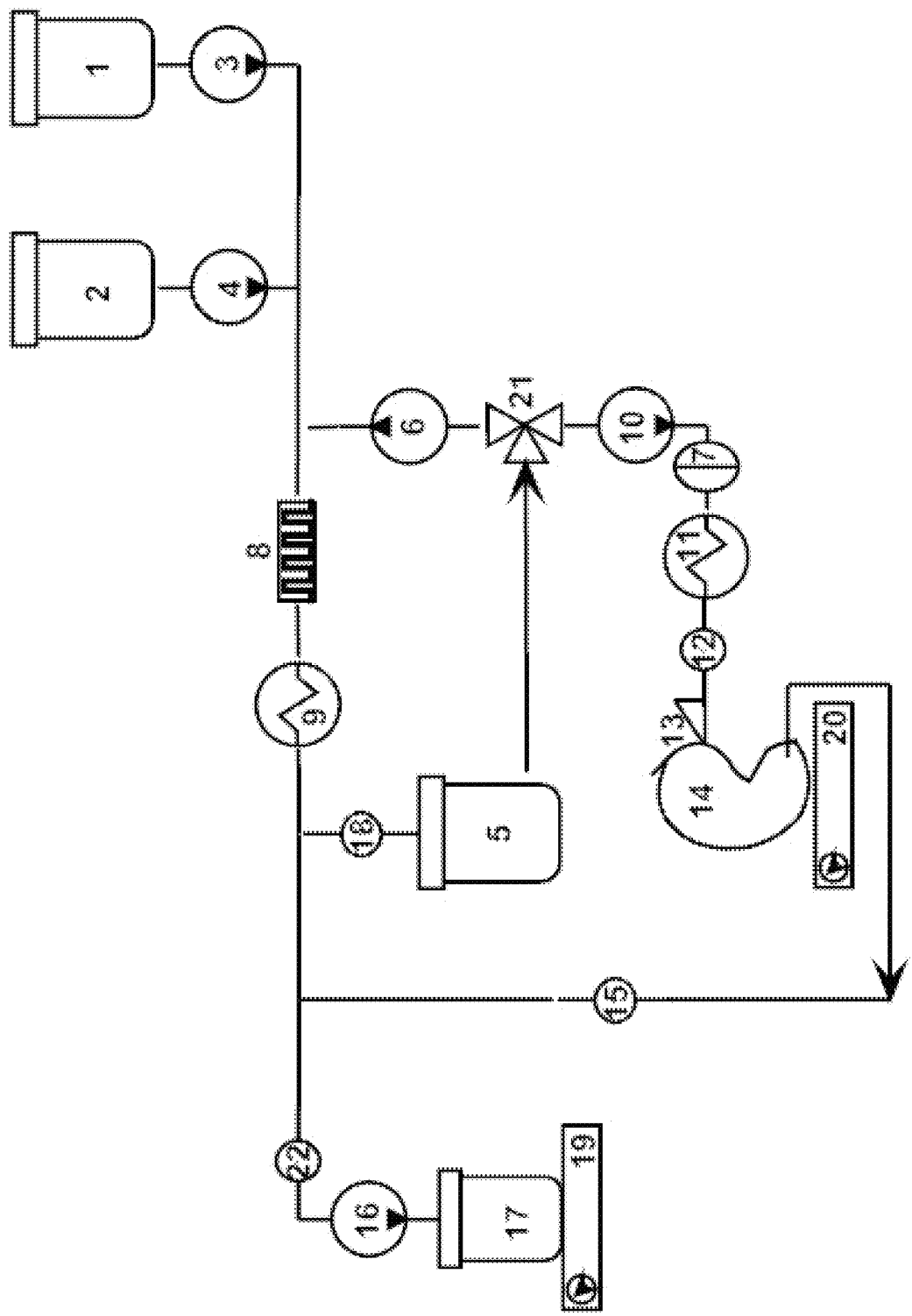

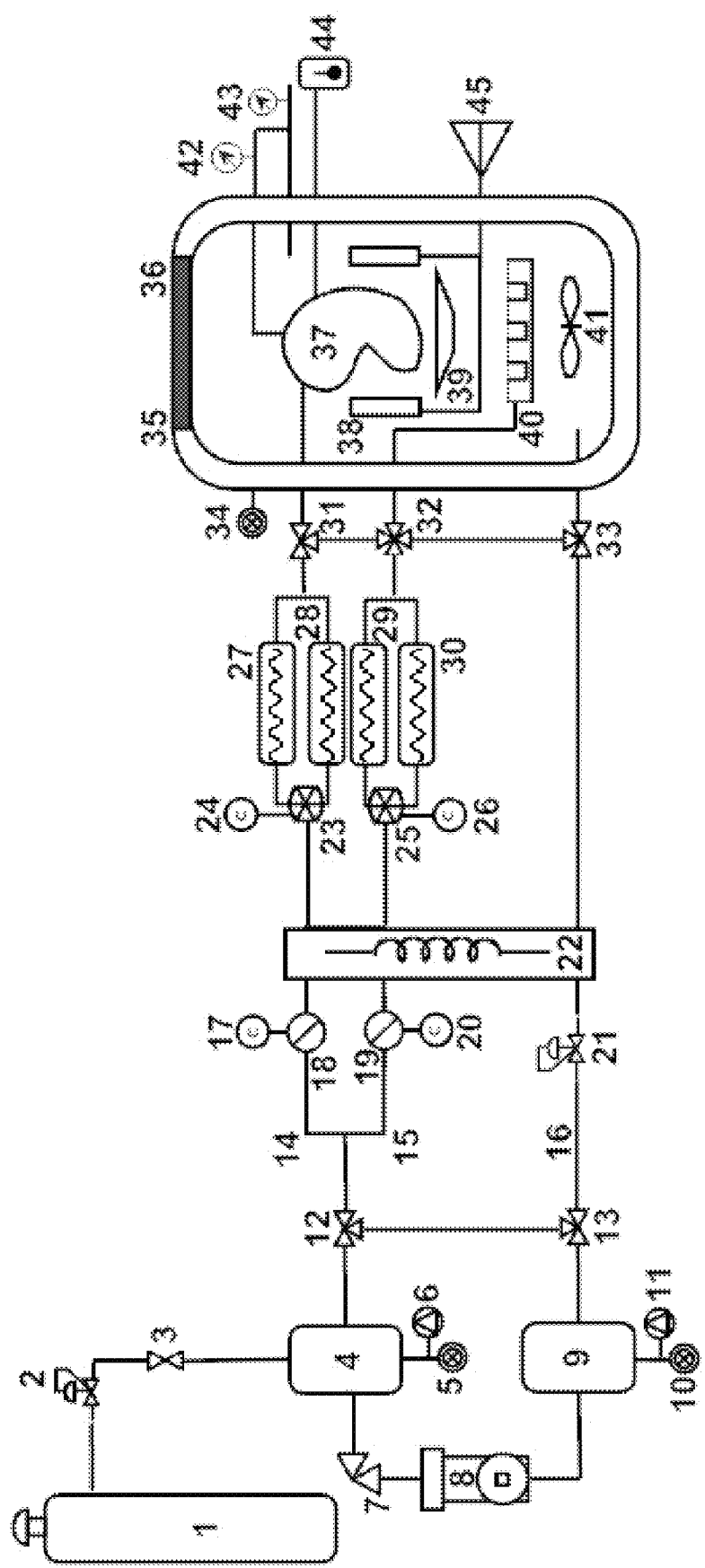
Figure 4: Persufflation Apparatus

METHOD AND APPARATUS FOR PREVENTION OF THERMO-MECHANICAL FRACTURING IN VITRIFIED TISSUE USING RAPID COOLING AND WARMING BY PERSUFFLATION

RELATED APPLICATION INFORMATION

This application claims the benefit of U.S. Provisional Application No. 61/805,875, filed on Mar. 27, 2013 and entitled Method and apparatus for prevention of thermo-mechanical fracturing in vitrified tissue using rapid cooling and warming by persufflation, U.S. Provisional Application No. 61/668,995, filed on Jul. 6, 2012 and entitled Method and apparatus for prevention of thermo-mechanical fracturing in vitrified tissue by composite cryoprotection, and U.S. Provisional Application No. 61/668,998, filed on Jul. 6, 2012 and entitled Rapid cooling of biological systems by gas persufflation under pressure, the entire contents of all which are hereby incorporated by reference. This application further is related to U.S. Provisional Application No. 61/495,386, filed on Jun. 10, 2011 and entitled Method and apparatus for prevention of thermo-mechanical fracturing in vitrified tissue by composite cryoprotection, and U.S. Provisional Application No. 61/495,391, filed on Jun. 10, 2011 and entitled Rapid cooling of biological systems by gas persufflation under pressure, the entire contents of both which are hereby incorporated by reference.

BACKGROUND OF THE INVENTION

1. Field of the Invention

The field of the present invention concerns and relates to cryopreservation devices and methods.

2. Description of Related Art

As for the related art, organs which are harvested for transplant often need to be preserved in functional and transplantable condition for a period of hours or days to allow transport to the recipient.

Most common current practices for preserving harvested organs for transplant use ultra-profound hypothermia (between 0 and 5 degrees C.) combined with replacing the blood and/or submerging the organ in an organ preservation solution that consists of water, electrolytes, sugars, colloids, buffers, free radical scavengers, and metabolic precursors or metabolic suppressors. Sometimes, the organ preservation solution is continuously or intermittently perfused through the organ. This perfusion may or may not include the use of a heat exchanger and/or oxygenator to control temperature and to support metabolism. Sometimes different solutions are used to initially flush the organ, to store the organ without perfusion, or to perfuse the organ during storage. These methods generally do not allow for storage for more than three days, and most often (depending on the organ) only a few hours.

Previous efforts to extend this time to weeks or months have failed. Freezing organs, in which temperature is lowered below 0 degrees C., has failed to preserve transplantable organs because of the formation of ice. The experimental use of cryoprotective agents that reduce (but do not eliminate) ice formation are common in the storage of sperm, bacterial or cell cultures, or very small tissues. These agents, including organic solvents like glycerol or dimethyl sulfoxide, work on small sample sizes, but have not appreciably improved prospects for frozen organ storage.

Supercooled storage, where temperature is reduced slightly below 0 degrees C. and where ice formation has been suppressed by natural solutes, sugars, ice blockers, or anti-freeze proteins, has been similarly unsuccessful.

There has been some experimental success with vitrification of complex vascular organs. Vitrified organs or tissues are loaded with a high enough concentration of cryoprotectant agents that no ice forms even when cooled below the glass transition temperature of water-cryoprotectant mixtures (often below −120 degrees C.). Ice formation is prevented by replacing half or more of the water in the tissues with single or mixtures of organic solvents that penetrate cell membranes (such as dimethyl sulfoxide or glycerol), agents that do not penetrate the cell membrane (such as sugars, sugar alcohols, starches, proteins, and polymers), and agents that directly prevent the growth of ice from nucleating sites (ice blockers and anti-freeze proteins). This is generally accomplished in vascular organs by perfusing a gradually increasing concentration of cryoprotectant. Rabbit kidneys loaded with enough cryoprotectant to vitrify have consistently survived and provided sole support after re-implantation into experimental animals. At least one rabbit has survived indefinitely on a single kidney that had been vitrified and cooled to the glass transition temperature. This result has proven difficult to reproduce reliably.

Another experimental method for organ preservation has been persufflation. Persufflation is the process of flowing a gas through the vasculature of an organ, rather than blood or some other fluid. Persufflation that used oxygen to support metabolism has had some success, but provides results no better than conventional organ preservation solutions and hypothermia. Persufflation with hydrogen sulfide or carbon monoxide to suppress mitochondrial respiration is currently being experimented with. At least one attempt has been made to use persufflation to cool organs for frozen storage, but this proved unsuccessful due to the inherent problems of frozen storage.

The fundamental problem with persufflation is that the length of time an organ can be stored is similar to methods using organ preservation solutions and hypothermia. Vitrification below the glass transition temperature can, on the other hand, permit storage for years or decades.

Two problems are known to exist in vitrified organs and tissues. First, is the formation of thermo-mechanical fractures around and below the glass transition temperature. In vascularized tissue, organs and organisms of a size greater than a few cubic centimeters, thermo-mechanical fractures consistently transect blood vessels sufficiently to prevent successful recovery upon rewarming. Second, the cryoprotectant solutions that permit cooling without ice formation are themselves toxic and cause biochemical damage that makes viable recovery of the organ difficult.

Thermo-mechanical fractures are created by differential contractions in the tissues; and they may be caused by differences in coefficients of expansion in different tissue types, different cryoprotectant concentrations, by thermal gradients, and perhaps by other means. Masses of vitrifiable tissues larger than a few cubic centimeters consistently develop these large-scale fractures.

The tendency of tissue to fracture increases proportionally with the volume or domain size of the tissue. Suggestions for storage at just below the glass transition temperature may reduce—but in practice do not eliminate—fractures. Temperatures very close to the glass transition may also permit the growth of ice nucleation points that can make viable recovery of the organ more difficult by increasing the likelihood of ice forming during both cooling and rewarming. Furthermore, temperatures at or near the glass transition point (often below −120 degrees C.) may be insufficient for long-term banking of vascularized tissue, organs or organisms.

Cryoprotectant toxicity includes but is not limited to dehydration, membrane damage, destabilizing and denaturing proteins, oxidative damage, and metabolic disruption. The extent of this damage is roughly proportional to the exposure time of biological tissue to cryoprotectant at a given temperature. Generally, the longer the exposure time and the higher the temperature, the greater the toxic damage. Conversely, cooling rapidly reduces both exposure time and temperature, reducing toxicity.

Additionally, with vitrifiable organs, there exist critical cooling rates below which ice forms, and above which ice does not form. Likewise, there are critical warming rates below which ice forms on warming and above which ice does not form. These critical cooling and warming rates depend on the concentration of cryoprotectant or vitrification solution. Therefore, increasing both cooling and warming rates can reduce cryoprotectant concentration, effectively reducing cryoprotectant toxicity. Since cryoprotectant toxicity increases non-linearly with concentration, even small reductions in concentration can yield large decreases in toxicity.

SUMMARY OF THE INVENTION

The present invention addresses these needs by providing for workable systems and low-temperature methods of storing tissues with little to no ice formation for long term stability without the creation of fractures that prevent revival and resuscitation. One feature of the invention entails rapid cooling and warming of biological systems via gas persufflation under pressure. Toxicity of cryoprotectants is attenuated by increasing cooling and/or warming rates, and by replacing the cryoprotectant in the vasculature of vitrified tissue, organ or organism with a non-toxic gas such as helium. Inert gases are preferred, due to their reduced reactivity with biological tissue Removal of the cryoprotectant from the organ vasculature will contribute to the reduction of toxicity because of the reduced exposure to the solutions.

When using a gas with a boiling point significantly below that of the glass transition temperature of the water/cryoprotectant solution, an extracorporeal heat exchanger can be used to cool the tissues from the inside, as opposed to current methods which use surface cooling methods exclusively.

Cooling at higher than atmospheric gas pressure can increase the density of the gas and thereby increase the rate of cooling to orders of magnitude beyond that of surface cooling. This increase in density (so long as it does not approach any phase transition for the gas used) does not increase the viscosity of the gas and yet allows for keeping the volumetric flow rate the same. This effectively increases the heat-carrying capacity of the gas, and increases the cooling rate in proportion to the increase in pressure.

A physical embodiment of this is can take the form of an extra-corporeal perfusion system, where the "fluid" to be pumped is a gas. This may be achieved by, or carry a requirement for, a pump or pressure infusion system with a volumetric rate 100 times or greater than that of a liquid. Included in this circuit can be a heat exchanger capable of removing heat at high rates and low temperatures. This heat exchanger may be cooled with a heat engine or by the evaporation of a cryogenic fluid or solid.

This invention encompasses methods for avoiding fracturing in vitrified biological systems that may occur in connection with cryoprotection procedures. One aspect can comprise a method and device for preventing thermo-mechanical fracturing in vitrified biological systems, e.g., organs, via rapid cooling and warming using persufflation. Another aspect may comprise a process and apparatus for prevention of thermo-mechanical fracturing in vitrified tissue using rapid warming, e.g., following cooling, via persufflation. The latter process and apparatus may further prevent thermo-mechanical fracturing in vitrified tissue using rapid cooling, e.g., prior to the rapid warming, by persufflation.

According to one feature, a system is provided for preventing gross fractures that transect blood vessels in biological tissue vitrified for storage or banking, whereby following the storage and banking the biological tissue can be removed in a relatively intact condition from storage, e.g., for transplant.

In accordance with one implementation of the invention a simplified perfusion system is provided. Its components can include one or more of a supply of fluid to be perfused, namely, a base perfusate reservoir 1, a pump to circulate the fluid effectively replacing the action of a beating heart, a heat exchanger/oxygenator to provide for cooling or warming of the fluid and oxygenation or other gas to support or reduce metabolism, an arterial cannula or other tube to provide arterial access to the vasculature of the organ of an animal or other biological tissue, a venous cannula for withdrawal of fluids, a return reservoir, and a return line.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically included, replicated and/or excluded, in any combination, in/from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description that follows.

BRIEF DESCRIPTION OF THE DRAWINGS

FIG. 1 is a simplified schematic diagram of a perfusion system according to an aspect of the invention;

FIG. 2 is a simplified diagram elucidating a persufflation process for cooling and rewarming organs according to the invention;

FIG. 3 depicts a perfusion system, as in FIG. 1, exemplified as a perfusion apparatus according to an embodiment of the invention; and FIG. 4 illustrates a persufflation and diathermy apparatus for deep cooling of a biological tissue such as an organ in accordance with the invention.

DETAILED DESCRIPTION OF THE INVENTION

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various cryoprotection and vitrification systems and other techniques that are conventionally used in the art, and only so much of the commonly practiced process steps and features are included herein as are necessary to provide an understanding of the present invention. The present invention has applicability in the field of organ and tissue preservation and processes in general.

An aspect of the invention is to enable reliable storage of organs for extended periods as compared to the current state of the art. For instance, periods can be extended beyond just several hours, days or a week, preferably for periods of time (months or years) adequate to enable proper banking, e.g., as is capable for blood products and other small tissues such as heart valves, cartilage, and skin. Such new forms of reliable banking according to the invention can permit expansion of supply for the world transplant market and/or relatively superior patient outcomes during transplantation. Improvements and/or advantages via the invention further constitute one or more of better immunological matching and optimized timing of the surgery, e.g., based on the recipient's medical condition.

For the purposes of this disclosure, "organ" includes any biological structure with a vascular system, such as solid organs, e.g., kidney, liver, heart, lungs, pancreas, brain, eyes, skin, muscles, all or part of the intestinal tract, limbs or portions of limbs, bio-artificial organs, cloned or cultured organs, decellularized extracellular matrices used to culture organs, artificial scaffolding for culturing organs, and entire organisms. Purposes for storing these organs can include curing disease, replacing damaged organs, improving function or enhancing organisms, extending lifespan or suspended animation for medical reasons, space travel, or other purposes.

In accordance with an aspect of the invention, a system is provided that cools vitrified vascular biological tissue by persufflation of the vasculature (flowing gas through the blood vessels instead of blood or other fluids) wherein the system uses helium gas, hydrogen gas, neon gas, argon gas, krypton gas, xenon gas, nitrogen gas, or mixtures of the same to cool and warm the tissue; and the system is operated under hyperbaric pressure to increase the density and heat-carrying capacity of the gas.

Additional gases that may be used for persufflation include any gas with a boiling point significantly below 0 degrees C., including hydrocarbons such as methane, ethane, propane and fluorinated compounds such as sulfur hexafluoride, fluorocarbons, perfluorocarbons, hydrofluorocarbons, chlorofluorocarbons, and hydrochlorofluorocarbons.

Referring more particularly to the drawings, FIG. 1 is a simplified schematic diagram of a perfusion system according to an aspect of the invention. Its components can include one or more of a supply of fluid to be perfused, namely, a base perfusate reservoir 1, a pump 2 to circulate the fluid effectively replacing the action of a beating heart, a heat exchanger/oxygenator 3 to provide for cooling or warming of the fluid and oxygenation or other gas to support or reduce metabolism, an arterial cannula or other tube 4 to provide arterial access to the vasculature of the organ of an animal or other biological tissue 5, a venous cannula 6 for withdrawal of fluids, a return reservoir 7, and a return line 8.

This invention refers to the storage of vascular tissues, vascular organs, brains, or whole animals, including human beings, at cryogenic temperatures. The tissues are perfused by a cryoprotectant solution that reduces or eliminates ice formation. This temperature is kept below the glass transition temperature of the tissue (often around −130 degrees C.) whereby storage at such a temperature can be extended to at least decades without significant deterioration in the tissue. A purpose of this storage can be organ and tissue banking for transplant purposes, or for eventual resuscitation in the case of whole animals and persons.

Tissues, organs, and whole animals and persons to be stored below the glass transition of water-based solutions are protected by replacing half or more of the water in the tissues with single or mixtures of organic solvents that penetrate cell membranes (such as dimethyl sulfoxide or glycerol), agents that do not penetrate the cell membrane (such as various large polymers), and agents that directly prevent the growth of ice from nucleating sites ("ice blockers"). The water that is replaced in both the extra and intra cellular is removed osmotically, and the cryoprotectants enter the tissues by diffusion. These cryoprotectant solutions are perfused through the vasculature, usually, but not necessarily, by cannulating the arterial and venous systems, and using a mechanical pump to replace the pumping action of the heart. In whole animals or humans, the central circulatory system by cannulating some combination of the aorta, vena cava, carotid artery, jugular vein, femoral artery and vein, as is done in cardiopulmonary bypass surgery, and often using the same equipment.

Once sufficient water has been replaced by cryoprotectant to ensure no ice formation occurs, the tissue, organ, or organism is then placed in a cold environment to cool externally. At this point in the process, the cryoprotectant remaining in the vasculature will be flushed out by a noble gas or inert gas that does not undergo any phase change at temperatures far below the glass transition, and possibly as low as that of liquid nitrogen. In addition to removing the remaining cryoprotectant, this gas is used to rapidly cool the tissue, organ or organism internally. Possibilities for the gas include but are not limited to hydrogen, helium, nitrogen, argon, neon, krypton, xenon, or mixtures of the same.

By replacing the volume of the vasculature (from 5 to 10 percent of the volume of tissues, organs, or whole organisms) with a gas, the vasculature itself becomes a "crush space" that allows stresses to be relieved by plastic deformation at a very small scale. This reduces the domain size of fracturing and effectively reduces the surface to volume ratio of even an entire human being to that of solid volume of a few cubic centimeters, the size of samples that have been successfully cooled to liquid nitrogen temperature without fracturing. Furthermore, any fractures that do begin will fail to propagate further than the next capillary and are incapable of transecting blood vessels. (This is similar to the fracture resistance exhibited by foamed metals and foamed silicate glass.) By using the vasculature for cooling rather than on or through the surface of the organ, temperature gradients are reduced throughout the organ, providing an additional reduction in the tendency to fracture. Computerized Tomography imaging indicates that our experiments swine kidneys are free of gross fractures down to at least the millimeter scale.

Once the inert gas has replaced the cryoprotectant in the vasculature, the tissue, organ, or organism can then be cooled to deep cryogenic temperature well below the glass transition temperature, including temperatures as low as that of liquid nitrogen or liquid helium. This cooling can be by persufflation alone or combined with surface cooling in a cold gas or liquid. A period of annealing at a temperature slightly above the glass transition temperature may be used during the cooling process.

Once cooled to well below glass transition, the system is stable for times on the order of decades to centuries.

FIG. 2 shows a simplified diagram of the persufflation method for cooling and rewarming organs according to the invention. In regard to persufflation cooling, this type of type of heat extraction, alone, can be problematic or sub-optimal, stemming from or relating to, for example, the low volumetric heat capacity of gases. With persufflation cooling, gas flow rates can be 200 times that of a liquid (having 200 times less viscosity), yet the volumetric heat capacity can be 1000 times less, yielding a cooling rate one-fifth of that of liquid perfusion cooling.

A feature of the present invention is to perform persufflation cooling e.g., as mentioned above using a higher than atmospheric gas pressure, to increase the density of the gas. Such an increase in density (so long as it does not approach any phase transition), does not increase the viscosity of the gas, so can be achieved while keeping the volumetric flow rate the same.

As a result of persufflation cooling under hyperbaric conditions, the heat capacity of the gas can effectively increased, whereby for instance the cooling rate can be increased in proportion to the increase in pressure. Since humans have lived and worked at pressures from 20 to 60 atmospheres during saturation diving at sea and experimentally on land, such pressures are readily survivable by organs.

Persufflation cooling under hyperbaric conditions also can be faster than perfusion cooling. Perfusion cooling must be done with low temperature liquids which become more viscous as temperature decreases. In contrast, as gases cool, they become less viscous, making persufflation at cryogenic temperatures much easier. Additionally, compounds that remain fluid at cryogenic temperatures tend to either be environmentally problematic, biologically toxic in their own right, or expensive. These problems do not exist for most inert gases useable for persufflation.

This rapid cooling can be several degrees per minute, or 10 to 100 times faster than surface cooling as is normally done with vitrifying organs. Therefore, the toxic damage from cryoprotectants that occurs during cooling can be 10 to 100 times less.

Both cryoprotectant toxicity damage and fracturing can occur on rewarming the organ to remove it from storage for transplant. Typically in vitrified organs, temperature has to increase at a faster rate than it was reduced to avoid the formation of ice. To accomplish this, warming can be assisted with heating by infrared light, radio frequency (RF) radiation, microwave radiation, or ultrasound. Past experience with these methods have lead to hot spots and runaway heating from heterogenous heating. However, persufflation redistributes the radiation heating more evenly over the organ, reducing or inhibiting temperature hot spots and runaway gradients.

Once the organ is warmed to a high enough temperature it can be perfused with cryoprotectant, then the cryoprotectant is removed the same way it was added, by perfusing while gradually decreasing the cryoprotectant concentration of the perfusate. Once all or most of the cryoprotectant has been removed, the organ can be reperfused with blood or blood substitute, and transplanted into the recipient.

Aspects of the invention include the following, in any combination, permutation, iteration and/or repetition: Long term tissue, organ or organism storage at or below the glass transition temperature combining vitrification using chemical cryoprotectants and persufflation with an inert gas. The chemical cryoprotectant is any liquid or gas that, when replacing part or all of the water in an organ or tissue, suppresses the formation of ice crystals. The organ or tissue is any organ or biological tissue with a vascular system, natural or artificial. An inert gas includes but is not limited to hydrogen, helium, nitrogen, argon, neon, krypton, xenon, hydrocarbons, sulfur hexafluoride, fluorocarbons, perfluorocarbons, hydrofluorocarbons, chlorofluorocarbons, hydrofluorocarbons, or mixtures of the same.

Additional aspects of the invention include the following, in any combination, permutation, iteration and/or repetition with the preceding: Persufflating cryoprotected organs or tissues with hydrogen sulphide, carbon monoxide, or other gas that will reduce or support metabolism, in a mixture with an inert gas. Non-inert gases such as oxygen or carbon dioxide may be used to support or modulate metabolism. By cooling to the glass transition temperature and below while persufflating, the vasculature is filled with gas. This prevents the formation of gross fracturing, and the propagation of any gross fractures that start is sharply limited. The volumetric heat capacity of the gas is increased by persufflating under hyperbaric conditions, thereby increasing cooling and warming rates above those performed at atmospheric pressure. Persufflating with gas colder than the organ will rapidly cool the organ. Persufflating with gas warmer than the organ will warm the organ. Cooling or warming by persufflation reduces temperature gradients within the cooling or warming organ or tissue, reducing gross thermo-mechanical fracturing and improving viability. Organs or tissues are cooled by both persufflation and surface cooling with cold inert gas or liquid. Organs or tissues may be held for a period of time slightly above the glass transition temperature during both cooling and warming to allow annealing and strain relief.

Continuing with the exemplary aspects, such further can include the following, in any combination, permutation, iteration and/or repetition: Cooling and warming an organ or tissue rapidly reduces the effective toxicity of cryoprotectants, and improves the viability of the organ or tissue. Combining persufflating with warm inert gas with heating by radio frequency diathermy, microwave diathermy, ultrasonic heating, or infrared heating to increase warming rate. Combining persufflation with warm gas with heating by radio frequency diathermy, microwave diathermy, ultrasonic heating, or infrared heating improves the uniformity of external heating and reduces or eliminates hot spots caused by radio frequency (RF) diathermy, microwave diathermy, ultrasonic heating, or infrared alone.

Perfusion Device

Once the organ has been removed from the donor, blood flushed out, and cooled to profound hypothermic temperature, it must be cryoprotected. This is done by perfusing a blood-like solution (with salts, sugars, and colloid) containing cryoprotectant of varying concentrations through the vasculature.

FIG. 3 is a diagram exemplifying a more typical embodiment of the Perfusion Apparatus, as compared to the simplified version set out in FIG. 1.

The cryoprotectant concentration of this loop is controlled by adding concentrated cryoprotectant 1 with the metering pump 3. Base perfusate 2 to reduce the concentration of cryoprotectant is added by metering pump 4. These additions are made to the recirculating loop composed of the recirculating pump 6, a heat exchanger 9, and a static mixer 8. The recirculating loop keeps the reservoir well mixed and prevents stratification of the cryoprotectant. The static mixer ensures the added base perfusate or cryoprotectant concentrate is well mixed into the reservoir; and the heat exchanger keeps the contents of the reservoir at an appropriate temperature. A sensor 18 is used to verify the concentration of the mixture that feeds into the main perfusate reservoir 5.

The concentration starts low and gradually increases over time in order to avoid osmotic damage to the organ. After the concentration of cryoprotectant in the organ is sufficiently high to cool to below the glass transition temperature of the vitrified tissue (which varies dependent upon the composition of the chosen cryoprotectant) without ice formation, the organ is then moved to the persufflation apparatus for deep cooling (c. "FIG. 4).

During recovery from storage the opposite is done. The organ is persufflated with warm gas to warm it sufficiently for perfusion. Reperfusion starts with a high concentration of cryoprotectant that is gradually decreased over time until all or most of the cryoprotectant is removed.

Perfusion cryoprotection begins with the organ being cannulated 13 at its main artery, and the cannula attached to the apparatus so the perfusate can flow into the artery. The organ is placed in a dish that gravity or pump feeds in the main perfusate reservoir 5. A closed fluid loop is formed by the tubing starting at the reservoir 5, to the arterial pump 10 which pumps the perfusate first through a medical heat exchanger/oxygenator 11, which controls the temperature and dissolved gases added to the cryoprotectant, through the sensor 12 that verifies the cryoprotectant concentration flowing into the organ 1, to another sensor 15 that monitors the cryoprotectant concentration that is removed from the organ via a venous cannula or gravity feed, and either returns that solution to the main perfusate reservoir 5 or to the waste reservoir 17.

To keep the level of cryoprotectant in the reservoir 5 even and to gradually remove used perfusate, another metering pump 16 removes fluid from the reservoir 5 cryoprotectant loop. The addition of old perfusate and addition of new perfusate is under computer control, to match a predetermined program of increasing or decreasing cryoprotectant concentration. A three-way valve 20 is used to regulate whether the cryoprotectant passes into the organ 14 or returns to the perfusate reservoir 5 or both. The concentration sensors 12, 15, 18 measure the concentration of cryoprotectant in the main loop, and the computer calculates the appropriate flow rates for the metering pumps to match the predetermined concentration schedule. The concentration sensors can determine concentration by measuring refractive index, speed of sound, viscosity, infrared spectrum, or some combination of these and other methods.

Total amount of cryoprotectant concentrate and base perfusate added are determined by metering pumps 3, 4 and concentration sensor 18, and together give the total amount of cryoprotectant and water added to the system and the total amount of water removed. A weight scale 20 permits the absolute concentration of cryoprotectant in the organ to be calculated. These figures are displayed, plotted, and recorded in real time by the control computer. Another scale 19 is used to monitor the cryoprotectant withdrawal.

Both the heat exchanger/oxygenator 11 and the recirculating loop heat exchanger 9 are fluid/fluid heat exchangers supplied with coolant provided by a heat sink/heat source, or by a mechanical recirculating chiller.

According to an aspect of the invention, a Perfusion Apparatus is provided. FIG. 3 elucidates an exemplary Perfusion Apparatus according to an embodiment of the invention.

A parts list for the depicted Perfusion Apparatus is as follows.

1. Cryoprotectant Concentrate Reservoir: Perfusion fluid with a concentration of vitrification solution equal to or higher than target concentration needed to vitrify.
2. Base Perfusate Reservoir: Perfusion fluid with zero concentration of cryoprotectant.
3. Cryoprotectant Metering Pump: Pump that adds a measured amount of high-concentration cryoprotectant, under computer control.
4. Base Perfusate Metering Pump: Pump that adds a measured amount of base perfusate, under computer control.
5. Perfusate Reservoir: Contains a reserve of cryoprotectant mixture to be perfused through the organ.
6. Recirculating pump: Pump that recirculates the fluid in 5 from bottom to top to keep the fluid thoroughly mixed.
7. Sterilizing filter: Filter to remove contaminants from the perfusate entering the organ.
8. Static Mixer: Precision engineered device for the continuous mixing of fluids introduced to the circuit using metering pumps 3 and 4.
9. Heat Exchanger: A fluid/fluid heat exchanger to cool or warm the perfusate from a liquid heat sink or recirculating chiller/heater.
10. Arterial Pump: Main pump to remove perfusate from 5 and circulate it through the vasculature of the organ 14.
11. Heat Exchanger/Oxygenator: A combination liquid/liquid heat exchanger and membrane oxygenator used to control perfusate temperature and to add or remove dissolved oxygen or other gas as needed to support metabolism.
12. Concentration Sensor: An inline sensor to measure the concentration of cryoprotectant in the perfusion fluid before it is perfused through the organ. Provides data and feedback to control metering pumps 3, 4, 6 and 10.
13. Arterial Cannula: Tubing that is surgically connected to the artery feeding blood or cryoprotectant to the organ 14.
14. Organ to be vitrified and cryopreserved.
15. Concentration Sensor: An inline sensor to measure the concentration of cryoprotectant in the perfusion fluid after it has passed through the organ. Provides data and feedback to control metering pumps 3, 4, 6 and 10.
16. Withdrawal pump: Metering pump under computer control that removes a measured amount of cryoprotectant from the perfusing loop in order to keep the fluid level in 5 stationary as additional perfusate is added by metering pumps 3 and 4.
17. Storage/waste reservoir for removed perfusate.
18. Concentration Sensor: An inline sensor to measure the concentration of cryoprotectant in the main perfusion loop. Provides data and feedback to control metering pumps 3, 4 and 6.
19. Weigh Scale: Scale that measures the mass of removed perfusate. In combination with the concentration sensor 22, provides data that determines the concentration of cryoprotectant in organ 14.
20. Weigh Scale: scale that measures the change in mass of the organ 14 from the addition of cryoprotectant and the removal of water.
21. Three-way valve to divert cryoprotectant to organ 14 for vitrification or to the perfusate reservoir 5 or both.
22. Concentration sensor: An inline sensor that is used to determine the concentration of cryoprotectant withdrawn from the circuit.

Persufflation Device

Referring to FIG. 4, a Persufflation Apparatus is shown comprising: a Gas supply 1, Pressure regulator 2, Valve 3, Gas supply reservoir 4, Pressure relief valve 5, Vent valve 6, Valve 7, Gas compressor 8, Gas return reservoir 9, Pressure relief valve 10, Vent valve 11, 3-way valve 12, 3-way valve 13, Vascular gas supply line 14, Pressure vessel environmental gas supply line 15, Gas return line 16, Flow controller computer connection 17, Vascular gas flow controller 18, Flow controller computer connection 19, Environmental gas flow controller 20, Precision back pressure regulator 21, Countercurrent heat exchanger 22, Temperature control diversion valve, servo 23, Servo valve computer connection 24, Temperature control diversion valve, servo 25, Temperature control diversion valve, servo 26, Coil in cold sink 27, Coil in heat sink 28, Coil in cold sink 29, Coil in heat sink 30, 3-way valve 31, 4-way valve 32, 3-way valve 33, Pressure relief valve 34, Pressure vessel 35, Pressure vessel window 36, Organ, tissue, or other biological material 37, Radio frequency diathermy antennas 38, Organ cradle 39, Environmental gas diffuser 40, Environmental gas stirring fan 41, Differential pressure sensors 42, Absolute pressure sensors 43, Organ temperature sensors 44, Radio frequency diathermy generator 45.

Once cryoprotection is complete (as defined by the cryoprotection achieving the concentration needed to vitrify) the organ or other vascular biological tissue 37 is placed in a hyperbaric chamber 35, capable of containing gas pressure up to 60 atmospheres. This hyperbaric chamber has a window 36 for direct observation of the organ and a pressure relief valve for safety 34. The organ is cannulated to the artery or the vein (depending on whether prograde or retrograde flow is desired) or both and connected to a temperature sensor 44. The cannula tubing passes through the wall of the pressure vessel to connect to the remainder of the persufflation apparatus.

To prepare the system, the helium or other inert gas source 1 is used to fill the feed reservoir tank 4 to a pressure above that desired in the pressure vessel 35. The feed reservoir has safety mechanisms in place, including a pressure relief valve 5 and vent valve 6. Inert gas flows through the feed, with regulated pressure 2 and the rate of flow controlled by valve 3.

Leaving the feed reservoir, the gas passes through a three-way valve that flows either in the direction of the organ 37 or is diverted to the gas return reservoir 9 via another three-way bypass valve 13. The gas return reservoir also has safety mechanisms in place, including a pressure relief valve 10 and vent valve 11. Exiting the gas return reservoir 9, the gas flows through a gas compressor 8. The gas compressor 8 is adjusted to maintain the pressure in the gas supply reservoir 4 above the hyperbaric chamber pressure and the pressure in the return pressure vessel 9 below the hyperbaric chamber pressure. Another valve 7 regulates when the compressed gas is delivered to the gas supply reservoir 4.

When flowing from the gas supply reservoir 4 toward the organ 37, the gas is delivered to both a vascular gas supply line 14 and an environmental gas supply line 15. Each of these lines has gas flow controllers 18, 19 which are computer-controlled 17, 20. The inert gas is chilled by the countercurrent heat exchanger 22 and then continues to the three way diversion valve 23, 25. This valve, by controlling the ratio of flow between the heating coils 28, 30 and the cooling coils 27, 29 controls the temperature of the inert gas. Flow of the gas is computer-controlled through the activation of a servo valve 24, 26. The gas supplies then pass through a three way valve set 31, 32 to flow directly into the hyperbaric chamber 35 and into the organ 37 directly.

A bypass line exists such that it is possible to divert gas from the vascular supply line 14, the environmental supply line 15 or both directly to the gas return line 16 This bypass line involves three valves 31, 32, 33.

To persufflate the organ, the three-way valve 31 is switched so flow is through the cannula connected to the kidney. Flow rates through the kidney can be manually or computer controlled by adjusting the valve 23, based on either flow rate as determined by flow meter 31, or by the difference in pressure between the cannula and the chamber pressure, as determined by the differential pressure sensor 43.

The temperature of the flow is controlled by the diversion valve 23, the flow rate by valve 31, and the hyperbaric chamber pressure by the pressure regulator 21. The pressure vessel itself has several features necessary to support persufflation both during cooling and rewarming. Radio-frequency diathermy antennas 38 are inside the chamber to enhance rewarming of the organ 38; and these antennas are fed by an external radio frequency diathermy generator 45. Also inside the chamber 35 are a cradle for the organ 39; an environmental gas diffuser 40 connected via the environmental gas supply line 15; an environmental gas stirring fan 41, and multiple temperature monitors for the organ and the environment 44 and multiple pressure sensors for the environment and the organ 43 as well as differential pressure sensors for each 42.

A process of practicing one or more aspects of the invention can comprise one or more of the following steps: An organ or tissue is harvested from donor. Blood is washed out of the vasculature of the organ with a blood substitute. The organ is vitrified by a cryoprotectant perfused through the vasculature, or by diffusion, or both. Cryoprotectant concentration is gradually increased over a period of minutes to hours to a concentration able to vitrify to avoid osmotic stress. The organ is persufflated at atmospheric pressure with an inert gas. The inert persufflation gas is enhanced with gases that inhibit metabolism (such as hydrogen sulfide or carbon monoxide) or enhance metabolism (such as oxygen or carbon dioxide), as needed. The organ is placed in a hyperbaric chamber to increase the pressure and density of the persufflating gas. The temperature of the gas is reduced below the organ's temperature to cool the organ. The organ is cooled externally by stirred cold gas or liquid. The organ is held for a period of time just above the glass transition temperature to allow annealing and strain relief.

The present invention implements one or more further steps as follows: The organ is cooled by persufflation and/or external cooling until it reaches the final storage temperature below the glass transition temperature. The organ or tissue is held at the storage temperature for an indefinite period of time. This may comprise any number of days, weeks, years, decades, or longer.

Once the organ is removed from storage, it can be warmed by persufflation and/or external warming until it reaches a temperature just above the glass transition temperature. The organ can be held at this, or at about this, temperature for a period of time, e.g., to allow annealing and strain relief.

According to an aspect and typical implementation of the invention, the organ is warmed by persufflation and/or external warming by stirred gas or liquid until it reaches a temperature that permits perfusion removal of the cryoprotectant. Radio frequency diathermy, microwave diathermy, ultrasonic heating, or infrared heating, are combined with the persufflation and surface warming to enhance evenness and speed of warming. The inert persufflation gas can be enhanced with one or more gases that inhibit metabolism (such as hydrogen sulfide or carbon monoxide) or enhance metabolism (such as oxygen or carbon dioxide), as desired, indicated or needed.

Once the target temperature is reached, the hyperbaric pressure, e.g., to the extent applied, c.f., supra, can removed, preferably gradually and/or sufficiently, e.g., so as to avoid gas emboli in the organ or tissue (i.e., "the bends"). The tissues, e.g., the vasculature, can then be perfused with cryoprotectant, displacing the gases in the vasculature. The concentration of cryoprotectant that is perfused can be gradually reduced, so as to remove the cryoprotectant in the organ or tissue.

According to a typical implementation of the process, all of the cryoprotectant is removed, after which the organ or tissue is reperfused, e.g., with warm, blood or blood-like artificial solution, and/or with metabolic enhancers or suppressors as determined, indicated or needed. The organ or tissue, at this stage and/or an earlier step, can then be further processed, e.g., transplanted into a recipient.

The intent accompanying this disclosure is to have each/all embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention. Corresponding or related structure and methods disclosed or referenced herein, and/or in any and all co-pending, abandoned or patented application(s) by any of the named inventor(s) or assignee(s) of this application and invention, are incorporated herein by reference in their entireties, wherein such incorporation includes corresponding or related structure (and modifications thereof) which may be, in whole or in part, (i) operable and/or constructed with, (ii) modified by one skilled in the art to be operable and/or constructed with, and/or (iii) implemented/made/used with or in combination with, any part(s) of the present invention according to this disclosure, that of the application and references cited therein, and the knowledge and judgment of one skilled in the art.

Conditional language, such as, among others, "can," "could," "might," or "may," unless specifically stated otherwise, or otherwise understood within the context as used, is generally intended to convey that embodiments include, and in other interpretations do not include, certain features, elements and/or steps. Thus, such conditional language is not generally intended to imply that features, elements and/or steps are in any way required for one or more embodiments, or interpretations thereof, or that one or more embodiments necessarily include logic for deciding, with or without user input or prompting, whether these features, elements and/or steps are included or are to be performed in any particular embodiment.

All of the contents of the preceding documents are incorporated herein by reference in their entireties. Although the disclosure herein refers to certain illustrated embodiments, it is to be understood that these embodiments have been presented by way of example rather than limitation. For example, any of the particulars or features set out or referenced herein, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated and disclosed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the inventive concepts set forth herein and parts thereof, in any permutation and/or combination, include the subject matter of any one or more of the mentioned features and aspects, in any permutation and/or combination.

What is claimed is:

1. A method for cryopreservation of vascularized tissue or an organ, by cooling by persufflation under hyperbaric conditions and warming by persufflation under hyperbaric conditions using external heating the method comprising:
   perfusing through a vasculature a chemical cryoprotectant that comprises a liquid that replaces part of the water in vascularized tissue thereby suppressing the formation of ice:
   cooling the vascularized tissue to below the glass transition temperature of the tissue using persufflation of an inert gas under hyperbaric conditions, wherein the cooling of the vascularized tissue under these conditions limits the formation and propagation of gross thermomechanical fractures;
   storing the vascularized tissue for a period of time;
   rewarming the vascularized tissue using hyperbaric persufflation of an inert gas and external heating until the tissue is sufficiently warm to allow liquid to flow through the vasculature: and
   removing the cryoprotectant by gradually restoring part or all of the water to the vascularized tissue by perfusing a physiological solution containing water.

2. The combination method according to claim 1, wherein the vascularized tissue is any organ or biological tissue with a vascular system, whether natural or artificial.

3. The method according to claim 1, wherein the first or second persufflation step is performed by persufflation of an inert gas comprising one or more of hydrogen, helium, nitrogen, argon, neon, krypton, or mixtures thereof.

4. The method according to claim 1, wherein inert gas used in the first or second persufflation step is mixed with oxygen, carbon dioxide, hydrogen sulfide, or carbon monoxide, to reduce or support metabolism upon rewarming.

5. The method according to claim 1, characterized by the vascularized tissue being cooled by both persufflation and surface cooling with cold inert gas or liquid.

6. The method according to claim 1, in which the vascularized tissue, for a period of time, is held close to but not at the glass transition temperature during cooling and warming to allow for one or more of annealing and strain relief.

7. The method according to claim 1, the external heating is selected from one or more of radio frequency diathermy, microwave diathermy, ultrasonic heating, or infrared heating to increase warming rate, whereby by combining persufflation with warm gas and heating by radio frequency diathermy, microwave diathermy, ultrasonic heating, or infrared heating.

8. The method as set forth in claim 1, wherein the vascularized tissue is an organ.

* * * * *